United States Patent [19]
Wollangk et al.

[11] 4,326,527
[45] Apr. 27, 1982

[54] MICROWAVE HEAT SETTING OF TAMPON

[75] Inventors: Edward G. Wollangk, Oshkosh; Amnuey Lilaonitkul, Appleton, both of Wis.

[73] Assignee: Kimberly-Clark Corporation, Neenah, Wis.

[21] Appl. No.: 153,010

[22] Filed: May 27, 1980

[51] Int. Cl.³ .............................................. A61F 13/20
[52] U.S. Cl. ...................................... 128/285; 28/118
[58] Field of Search ................... 128/263, 285; 28/118, 28/120

[56] References Cited

U.S. PATENT DOCUMENTS

| | | | |
|---|---|---|---|
| 2,976,579 | 3/1961 | Rakll | 28/118 |
| 3,382,542 | 5/1968 | Witschi et al. | 28/118 |
| 3,606,643 | 9/1971 | Mooney | 28/119 |
| 3,738,364 | 6/1973 | Brien et al. | 28/120 |
| 4,081,884 | 4/1978 | Johst et al. | 28/119 |
| 4,128,692 | 12/1978 | Reid | 128/284 |

*Primary Examiner*—James J. Bell
*Attorney, Agent, or Firm*—Howard Olevsky; William D. Herrick

[57] ABSTRACT

A heat-set radially compressed tampon is made by radially compressing a prehumidified tampon pledget having absorbent fibers subjecting the compressed pledget to microwave heating.

7 Claims, 1 Drawing Figure

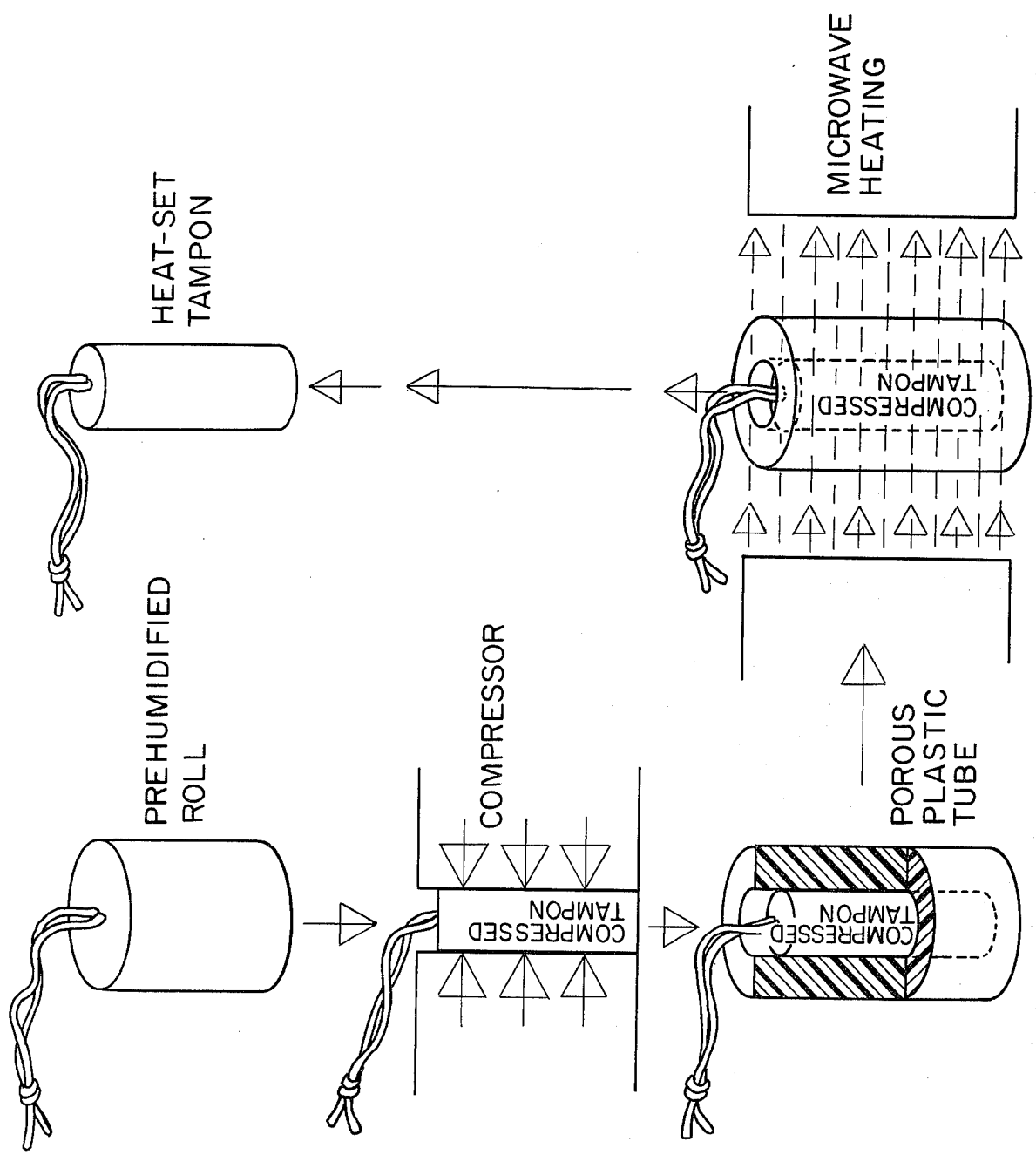

MICROWAVE HEAT SETTING OF TAMPON

FIELD OF THE INVENTION

The subject invention relates to tampons and particularly to compressed tampons.

BACKGROUND OF THE INVENTION

Compressed tampons have certain advantages over noncompressed tampons relating essentially to their increased absorbent material per unit volume, and accompanying ease of insertion relative to the amount of absorbent.

A radially compressed tampon, for instance, when in place in the vagina, radially expands with the uptake of menstrual fluid and may, in fact, swell to its original uncompressed volume or, in some instances, to an even higher volume.

Radially compressed tampons may be designed for digital insertion or for use with insertion aids such as the traditional telescoping tube type tampon applicator or the stick tampon applicator. In any event, after compression, the tampon pledget tends to reexpand to its original dimension. To overcome this tendency, heat-setting has been utilized. The application of heat is designed to "set" the tampon in its compressed state. Conventional heat-setting, however, has some distinct disadvantages. First and foremost of these is the substantial increase in manufacturing time necessary to subject the tampons to an amount of heat necessary to obtain some level of set. If relatively high temperatures are used in an attempt to speed the process, the outside of the tampon which is a dense, compacted material is heated substantially faster than the inside, and the outer surface may be degraded and lose its absorbent characteristics.

This invention provides a process for rapid and uniform heat-setting of a tampon containing fibrous absorbent as well as a radially compressed tampon having certain unique characteristics.

For purposes of this invention, the term "fibrous" refers to tampon absorbent material derived from traditional cellulosic sources such as wood pulp cotton linters, etc. as well as the rayon derived absorbents and certain synthetic absorbent polymeric fibers and is meant to include various mixtures of absorbent materials and blends which, for example, may include superabsorbents. The term is specifically used to differentiate between tampons which utilize a foam or a foam in combination with superabsorbents as the absorbent material. The teachings of this invention have no particular application to such nonfibrous absorbent materials.

SUMMARY OF THE INVENTION

According to the teachings of this invention, a process for rapidly and uniformly heat-setting a radially compressed tampon is provided which generally involves the steps of radially compressing a prehumidified tampon subjecting the compressed tampon to microwave heating while the tampon is preferably in an open-ended tube having openings disposed about the longitudinal axis thereof to heat-set the tampon pledget. The microwave chamber may be equipped with means for dry circulation or mild vacuum to remove the excess moisture. The tampon may then be packaged or placed into a tampon applicator tube for subsequent packaging.

DETAILED DESCRIPTION OF THE INVENTION

The general process of the subject invention can be readily understood by reference to the process flow schematic of FIG. 1. FIG. 1 shows the prehumidified tampon roll being subjected to compressive forces, insertion in a microwave transparent tube, and its exposure to microwave heating. This is the basic process of this invention.

While the concept of microwave heating per se is known, successful application of microwave heating to heat-set compressed tampons required the discovery and utilization of several unique and interrelated factors. It was necessary, first, to identify the need to have a sufficient amount of moisture present in the tampon to allow for efficient and successful microwave heating. The microwave heat-setting mechanism of the process of this invention realizes the difference between the molecular absorption of microwave energy between the moisture present within the tampon and the tampon fibers themselves. The water molecule preferentially absorbs microwave energy and does so essentially instantaneously and uniformly throughout the density of the tampon as soon as the microwave energy field is applied. Since the water molecules are essentially evenly distributed throughout the tampon, the entire tampon is heated in a relatively short period of time by a thermal conduction mechanism. It has been found that it is necessary, at the minimum, for the tampon to absorb sufficient moisture so that it has at least 10% moisture content based upon dry weight. Values of 12%-16% moisture by weight are currently preferred. Currently, this is accomplished by placing the tampon pledget in a humidification chamber maintained at 75° F. and having relative humidity of 80% until the tampon is in moisture equilibrium with the chamber. The time for equilibrium varies with the particular pledget materials chosen but generally is in the range of 18 to 26 hours. Of course, direct immersion in water is impractical because of the amount of time which would be required to dry the pledget to a workable moisture level.

An additional unique feature of this invention is the utilization of microwave transparent tubes having openings disposed along the longitudinal axis as well as at the top and/or bottom of the cylinder. Uniform removal of moisture at a rate rapid enough to be commercially utilized is obtained by employing the tubes in this step.

When the tampon of this invention has been treated as indicated particularly and necessarily from the standpoint of the product of this invention with means for the removal of excess moisture, it provides a tampon in which, it is theorized, substantial interstitial voids occur. These voids are created by the removal of moisture and provide additional sites for rapid fluid uptake. Also, as a result of water molecule excitation and evaporation, interfibrillar hydrogen bonding takes place as opposed to hydrogen bonding incorporating water molecules. This is a continuing process and actually speeds the removal of intra-tampon moisture as compared to conventional heating mechanisms. The existence of such interfibrillar bonding as well as interstitial voids is thought to overcome one of the primary disadvantages associated with radially compressed tampons and that is the initial slowness in fluid uptake until the radial compression is overcome. By the provision of essentially uniformly dispersed interstitial voids, sites are provided for rapid fluid uptake which would subsequently break down the interfibrillar bonding and create additional sites for fluid uptake. This would allow the radial reexpansion of the tampon much more rapidly than has been accomplished in the past and, therefore, provide for the full utilization of the absorptive capacity obtained by the radial compression in a much shorter period of time. Initial fluid uptake is further enhanced because of the rapid rupture of the interfibrillar hydrogen bonding. Such a design would also tend to prevent so-called early leakage associated with fluid flow around the edges of the radially compressed, unexpanded tampon when first inserted.

It is, of course, desirable that a tampon be prevented from premature expansion due to moisture uptake from the surrounding environment. This can be accomplished in a variety of ways such as controlling the humidity in the environment after the dehydration is completed and/or packaging the tampon relatively rapidly. It should be noted that while the dry tampon is more highly receptive to moisture than the prewet or nondry tampon, vapor uptake is hardly instantaneous. Furthermore, the relatively concentrated and uniformly distributed interfibrillar hydrogen bonding inside the tampon resulting from the heat-setting process of this invention would provide the tampon with the ability to prevent premature expansion due to vapor uptake from the surrounding atmosphere. The combination of the prehumidification and the application of microwave energy also provides for a uniform distribution of residual moisture in the tampon after the microwave treatment.

What is claimed is:

1. A process for heat-setting a radially compressed tampon comprising:
    (a) compressing a prehumidified tampon; said compressed tampon having a diameter less than its height;
    (b) inserting said compressed tampon in an open ended microwave transparent tube having openings along the longitudinal axis of said tube;
    (c) subjecting said tampon to microwave heating; and
    (d) drying said tampon.
2. The process according to claim 1 wherein the tampon is humidified to at least 10% of the dry weight.
3. The process according to claims 1 or 2 in which the tampon is inserted into an applicator after cooling and moisture removal is complete.
4. The process according to claim 1 in which the openings provide a substantially uniform exposed area around the tampon periphery.
5. The process according to claim 1 wherein the tampon is humidified to between 12% and 16% of its dry weight.
6. A tampon formed by the process of claim 1 characterized by the presence of substantially uniformly distributed interabsorbent moisture.
7. The tampon according to claim 6 wherein the absorbent includes superabsorbent material.

* * * * *